US006878383B2

(12) United States Patent
Boss, Jr. et al.

(10) Patent No.: US 6,878,383 B2
(45) Date of Patent: Apr. 12, 2005

(54) COMPOSITIONS FOR REGENERATING TISSUE THAT HAS DETERIORATED, AND METHODS FOR USING SUCH COMPOSITIONS

(75) Inventors: William K. Boss, Jr., Essex Fells, NJ (US); Olga Marko, Paramus, NJ (US)

(73) Assignee: Isolagen Technologies, Inc., Houston, TX (US)

( * ) Notice: Subject to any disclaimer, the term of this patent is extended or adjusted under 35 U.S.C. 154(b) by 116 days.

(21) Appl. No.: 10/167,173

(22) Filed: Jun. 11, 2002

(65) Prior Publication Data

US 2003/0228286 A2 Dec. 11, 2003

Related U.S. Application Data

(63) Continuation of application No. 09/678,047, filed on Oct. 3, 2000, now Pat. No. 6,432,710, which is a continuation-in-part of application No. 09/316,245, filed on May 21, 1999, now abandoned, which is a continuation-in-part of application No. 09/083,618, filed on May 22, 1998, now abandoned.

(51) Int. Cl.$^7$ .......................... A61F 13/00; A61F 2/00; A01N 65/00; C12N 5/02; C12N 5/06
(52) U.S. Cl. ...................... 424/422; 424/93.1; 424/424; 435/325; 435/363; 435/366
(58) Field of Search ................. 435/366, 325, 435/363; 424/422, 426, 93.1

(56) References Cited

U.S. PATENT DOCUMENTS

| | | | | |
|---|---|---|---|---|
| 4,485,097 A | * | 11/1984 | Bell | 424/549 |
| 4,835,102 A | | 5/1989 | Bell et al. | 435/29 |
| 4,940,666 A | * | 7/1990 | Boyce et al. | 435/371 |
| 4,963,489 A | | 10/1990 | Naughton et al. | 435/240.1 |
| 5,002,071 A | | 3/1991 | Harrell | 128/897 |
| 5,106,949 A | | 4/1992 | Kemp et al. | 530/356 |
| 5,110,604 A | | 5/1992 | Chu et al. | 424/484 |
| 5,166,187 A | | 11/1992 | Collombel et al. | 514/21 |
| 5,246,457 A | * | 9/1993 | Piez et al. | 424/423 |
| 5,282,859 A | | 2/1994 | Eisenberg | 623/11 |
| 5,292,655 A | | 3/1994 | Wille, Jr. | 435/240.2 |
| 5,308,764 A | | 5/1994 | Goodwin et al. | 435/240.24 |
| 5,591,444 A | | 1/1997 | Boss, Jr. | 424/426 |
| 5,660,850 A | | 8/1997 | Boss, Jr. | 424/426 |
| 5,665,372 A | | 9/1997 | Boss, Jr. | 424/426 |
| 5,691,397 A | * | 11/1997 | Glimcher et al. | 523/115 |
| 5,711,957 A | | 1/1998 | Patat et al. | 424/422 |
| 5,800,541 A | * | 9/1998 | Rhee et al. | 424/423 |
| 5,858,390 A | * | 1/1999 | Boss, Jr. | 424/426 |
| 5,885,829 A | | 3/1999 | Mooney et al. | |
| 6,432,710 B1 | * | 8/2002 | Boss et al. | 435/366 |

FOREIGN PATENT DOCUMENTS

| | | | | |
|---|---|---|---|---|
| WO | WO 85/04185 | 9/1985 | | C12N/5/00 |
| WO | WO 88/03785 | 6/1988 | | A61B/19/00 |

OTHER PUBLICATIONS

WK Boss, Jr et al., Clinics in Plastic Surgery, "Autologous Cultured Fibroblasts as Cellular Therapy in Plastic Surgery," Oct. 2000, vol. 27, No. 4, pp. 613–626.*
JF Hansbrough et al., Surgery, "Evaluation of a biodegradable matrix containing cultured human fibroblasts as a dermal replacememt beneath meshed skin grafts on athymic mice," 1992, 111: 438–446.*
CJ Doillon et al., Scanning Microscopy, "Fibroblast and Epidermal Cell–type I Collagen Interactions: Cell Culture and Human Studies," Jun. 1988, vol. 2, No. 2, pp. 985–992.*
S Mizuno et al., Experimental Cell Research, "Chondroinduction of Human Dermal Fibroblasts by Demineralized Bone in Three–Dimensional Culture," (1996)227: 89–97.*
CS Maas et al., Dermatol Surg, "Complications of injectable synthetic polymers in facial augmentation," Oct. 1997, 10:871–7.*
Feng et al, J Formosan Med Assoc 1992;91:1068–74.*
Kay et al, Pract Periodontics Aesthet Dent Mar. 1997;9:185–94.*
Alberts et al., *Molecular Biology of the Cell*, 2$^{nd}$ Edition, Garland Publishing, Inc. (NY and London), 1992, Chapter 17, pp. 987–988.
Cendron et al., "The Biological Behavior of Autologous Collagen Injected Into the Rabbit Bladder," The Journal of Urology 154:808–811, 1995.
Chung et al., "Enhanced proliferation and collagen synthesis of human dermal fibroblasts in chronically photodamaged skin," Photodermatol. Photoimmunol. Photomed. 12:84–89, 1996.
Ciancio et al., "Recent Advances in Periodontal Diagnosis and Treatment: Exploring New Treatment Alternatives," JADA 123:34–43, 1992.
Davidson, "Wound Repair," in *Inflammation: Basic Principles and Clinical Correlates*, 2$^{nd}$ Edition, Gallin et al., Editors, Raven Press, Ltd., NY, 1992, Chapter 39, pp. 809–819.
DeVore et al., "Effectiveness of injectable filler materials for smoothing wrinkle lines and depressed scars," Medical Progress through Technology 20:243–250, 1994.

(Continued)

*Primary Examiner*—Q. Janice Li
(74) *Attorney, Agent, or Firm*—Fish & Richardson P.C.

(57) ABSTRACT

The invention provides a composition for promoting regeneration of tissue which has degenerated in a subject as a result of a disease or disorder and a method of using the composition is provided. The composition comprises a biodegradable acellular matrix, and passaged autologous fibroblasts substantially free of immunogenic proteins, e.g., culture medium serum-derived proteins, integrated within the matrix. Also provided is an injectable composition comprising an acellular filler material (e.g., any type of collagen) and passaged autologous fibroblasts substantially free of immunogenic proteins, e.g., culture medium serum-derived proteins, for correcting defects in skin, such as wrinkles or scars, and for augmenting tissue in the subject, particularly facial tissue.

16 Claims, No Drawings

OTHER PUBLICATIONS

Ford et al., "Autologous Collagen Vocal Fold Injection: A Preliminary Clinical Study," Laryngoscope 105:944–948, 1995.

Grosh et al., "Variables affecting the results of xenogenic collagen implantation in an animal model," Journal of the American Academy of Dermatology 13:792–798, 1985.

Heimbach et al., "Artificial Dermis for Major Burns," Ann. Surg. 208:313–320, 1988.

Ishikawa et al., "Morphological and biochemical analyses on fibroblasts and self–produced collagens in a novel three–dimensional culture," British Journal of Dermatology 136:6–11, 1997.

Jeffcoat et al., "Evidence–Based Periodontal Treatment, Highlights from the 1996 World Workshop in Periodontics," JADA 128:713–724, 1997.

Lamme et al., "Living Skin Substitutes: Survival and Function of Fibroblasts Seeded in a Dermal Substitute in Experiental Wounds," J. Invest. Dermatol. 111:989–995, 1998.

Lattari et al., "The Use of a Permanent Dermal Allograft in Full–thickness Burns of the Hand and Foot: A Report of Three Cases," Journal of Burn Care & Rehabilitation 18:147–155, 1997.

Morgan et al., "Bioengineered Skin Substitutes," Science and Medicine, Jul./Aug. 1997, pp. 6–15.

Morris et al., "Early Clinical Experience with Topical Collagen in Vascular Wound Care," J WOCN 21:247–250, 1994.

Moy et al., "Glycolic Acid Modulation of Collagen Production in Human Skin Fibroblast Cultures In Vitro," Dermatol. Surg. 22:439–441, 1996.

Perricone, "An Alpha Hydroxy Acid Acts as an Antioxidant," J Ger Derm 1(2):101–104, 1993.

Postlethwaite et al., "Fibroblasts and Matrix Proteins," in *Fibroblasts and Matrix Proteins, Basic Principles and Clinical Correlates*, $2^{nd}$ ed., Raven Press:NY, 1992, pp. 747–773.

Sheridan et al., "Artificial skin in massive burns—results to ten years," Euro. J. Plast. Surg. 17:91–93, 1994.

Wainwright et al., "Clinical Evaluation of an Acellular Allograft Dermal Matrix in Full–Thickness Burns," J. Burn. Care. Rehabil. 17:124–136, 1996.

Medical Technologies, MedPro Month, Mar. 1997, p. 69.

Gelstlich Biomaterials, Bio–Oss®, one page, Apr. 1998.

Integra™ Artifical Skin Dermal Regneration Template, 1996 Integra LifeSciences Corporation, 6 pages.

Product Description, Calcitek, Colla–Tec, Inc. Catalog. 1995, 4624, BioMend, 4 pages.

Product Description, Calcitek, Colla–Tec, Inc. Catalog, 1993, 4608, Absorbable Collagen Wound Dressings for Dental Surgery, 2 pages.

Integra LifeScience Co. Catalog, 1995, Integra™ Artifical Skin, 5 pages.

Bio–Gide®, Osteohealth Company, IN8026, Jun. 1997, 2 pages.

* cited by examiner

COMPOSITIONS FOR REGENERATING TISSUE THAT HAS DETERIORATED, AND METHODS FOR USING SUCH COMPOSITIONS

This application is a continuation and claims priority of U.S. application Ser. No. 09/678,047, filed Oct. 3, 2000 now U.S. Pat. No. 6,432,710, which is a continuation-in-part and claims priority of U.S. application Ser. No. 09/316,245, filed May 21, 1999, now abandoned, which is a continuation-in-part and claims priority of U.S. application Ser. No. 09/083,618, filed May 22, 1998, now abandoned. U.S. application Ser. Nos. 09/678,047, 09/316,245, and 09/083,613 are incorporated herein by reference in their entirety.

FIELD OF THE INVENTION

The present invention concerns the regeneration of tissues in a subject that have degenerated as a result of a disease or disorder in the subject. More particularly, the present invention concerns novel compositions for use in surgical and nonsurgical techniques that promote regeneration of tissue whose mass has been diminished due to a disease or disorder in a subject, correct defects in the skin of subjects, or augment tissue in subjects. Also disclosed is the use of a novel composition in conjunction with a biodegradable acellular matrix for ameliorating defects in the tissues, and methods for using the novel composition.

BACKGROUND OF THE INVENTION

"Periodontal disease" is the term commonly used to describe inflammatory disease of the periodontium, i.e., the tissue surrounding and securing teeth to the jawbone. The condition is characterized by inflammatory and degenerative processes that develop at the gingival margin (gingivitis) and lead to a progressive breakdown and resorption of the periodontal ligament and bone (periodontitis), oftentimes resulting in severe diminution of the periodontium. Periodontal disease is the leading cause of tooth loss in adults after middle age. [Anderson's Pathology, p. 2000, John M. Kissane ed., 9th ed. (1992)].

Periodontal disease results from the accumulation of bacterial plaque in the gap between the gingiva and the tooth. While anaerobic bacteria are the primary etiologic agents, the destructive process is believed to be mediated in large part by immunologic reactions of the host. As the disease progresses, a periodontal pocket is established below the gingival margin, thus prolonging and promoting the inflammatory process. Successive inflammatory reactions result in the progressive erosion of the tooth-supporting tissues, i.e., the collagenous fibers making up the periodontal ligament and the bone pocket in which the tooth sits. [Reviewed in Anderson's Pathology, pp. 1999-2000, John M. Kissane ed., 9th ed. (1992); Shafer et al., A Textbook of Oral Pathology, 4th ed. (1983)].

Periodontal disease can be diagnosed by checking the gingiva for inflammation, probing the depths of periodontal pockets, checking clinical attachment level, and assessing bone loss by means of autoradiography. [Jeffcoat, M. K., et al., J. Am. Dent. Assoc., 128:713–724 (1997)].

A number of techniques, both surgical and nonsurgical, have been developed to treat periodontal disease. Particularly with respect to severe periodontitis, none of the currently available treatments are wholly satisfactory.

For relatively mild cases of periodontitis, practitioners have traditionally employed nonsurgical mechanical debridement (i.e. scaling and root planing) to remove the bacterial plaque whose accumulation perpetuates the disease, thereby reducing inflammation. Mechanical debridement can be accomplished using manual, sonic or ultrasonic instruments. Scaling and root planing have been shown to decrease gingival inflammation, decrease probe depth, and promote maintenance of clinical attachment level. However, without resorting to surgical procedures, access to root surfaces and bony defects is restricted, and only limited debridement is possible. [Jeffcoat, M. K., et al., J. Am. Dent. Assoc. 128:713–724 (1997)].

As a result, nonsurgical scaling and root planing is insufficient to treat more severe cases of periodontitis, and it is necessary to resort to more aggressive surgical techniques. Surgical techniques comprise reflecting the gingival tissues to provide access to root surfaces and bone defects, in order that mechanical debridement may be accomplished directly. Following debridement, the gingival tissue is sutured back in position. Currently available surgical approaches entail substantial patient discomfort and fail to consistently provide satisfactory outcome.

There are a number of non-surgical, non-mechanical approaches to treating periodontal disease, including supragingival and subgingival irrigation and the application of chemical and antimicrobial agents. Yet none of these approaches have achieved more than marginal success [Jeffcoat, M. K., et al., J. Am. Dent. Assoc., 128:713–724 (1997)]. In particular, there are a number of deleterious side effects associated with the use of antibiotics, along with risks such as drug sensitivity and the emergence of antibiotic-resistant pathogens.

Another approach to combating destruction of the periodontal tissue has focused on inhibiting the matrix metalloproteases responsible for this destruction. Tetracyclines in particular have shown promise as inhibitors of extracellular collagenases, but cause the same side effects associated with antibiotics in general. Modified forms of tetracycline have been developed which are non-antimicrobial and retain their ability to inhibit collagenases, but these chemically modified tetracyclines are not commercially available. [Ciancio, G. C. et al., J. Am. Dent. Assoc. 123:34–43 (1992)].

Because cell proliferation, cell migration and matrix synthesis are prerequisites for periodontal regeneration, some researchers have attempted to use tissue growth factors, for example insulin-like growth factor, platelet-derived growth factor, and transforming growth factor to promote periodontal regeneration.

In summary, none of the nonmechanical approaches to treating periodontitis have been able to offer more than modest, short term enhancement of traditional mechanical debridement. As noted in a 1997 review of techniques used in treating periodontal disease, "scaling and root planning accompanied by oral hygiene procedures remains the first mode of treatment for adult periodontitis." [Jeffcoat, M. K. et al., J. Am. Dent. Assoc., 128:713–724 (1997)].

A great deal of research has been directed to methods of regenerating periodontal tissue lost as a consequence of periodontal disease, but as yet no wholly satisfactory method is available. For the most part, efforts have focused on surgical approaches that fill the defects with a variety of materials (bone grafting) or use guided tissue regeneration.

Bone grafting techniques involve the use of natural bone or synthetic bone materials. Natural bone grafts are typically either autografts (grafts transferred from one position in the body of a patient to another position in the body of the same patient) or allografts (grafts transferred from one person to another). Clinicians using natural bone grafts have had limited success in inducing new bone growth. Problems associated with the use of autografts include the need for a second surgical site and, in some cases, fresh grafts may be associated with root resorption. [Jeffcoat, M. K. et al., J. Am. Dent. Assoc. 128:713–724 (1997)].

Freeze-dried, demineralized bone has been used as an allograft and shown to promote bone formation. However, the predictability and the amount of bone fill achieved varies. [Jeffcoat, M. K. et al., J. Am. Dent. Assoc., 128:713–724 (1997)]. Since allografts are transferred from one person to another, the potential exists that viruses or other pathogens might be transferred to the patient.

Synthetic bone materials which have been investigated include plaster, calcium carbonates, and ceramics such as hydroxyapatite. Clinical trials have demonstrated that the use of synthetic grafts has resulted in improvements in probing depth and attachment level. Histologic findings, however, indicate that, in general, synthetic grafts act primarily as space fillers, with little if any regeneration. [Jeffcoat, M. K. et al., J. Am. Dent. Assoc., 128:713–724 (1997)].

Guided tissue regeneration is a surgical approach based on placing a membrane barrier under a soft tissue flap above the area of bone loss to enhance wound healing potential. [Ciancio, G. C. et al., J. Am. Dent. Assoc., 123:34–43 (1992]). Investigators have studied both resorbable and nonresorbable membranes. A significant disadvantage of using a nonresorbable membrane is the requirement of a second surgical procedure after approximately six weeks to remove the membrane. Furthermore, in about 40%–50% of the cases, such membranes become infected in the patient. While less evidence is available for resorbable membranes than for nonresorbable membranes, improvements in clinical attachment levels have been shown for both types of membranes compared with debridement alone. Most favorable results are reported for Class II furcations in the mandible and for intrabony defects. Less favorable results have been reported in maxillary molar and Class III (through and through) furcation defects. [Jeffcoat, M. K. et al., J. Am. Dent. Assoc., 128:731–724 (1997)].

In summary, none of the currently available treatments for periodontal disease is wholly satisfactory, particularly with regards to regenerating periodontal tissue lost as a result of periodontitis.

The oral mucosa is the tissue lining the oral cavity. There are a number of conditions that can result in defects in the oral mucosa, for example trauma, dermatoses, recurrent aphthous stomatitis, and infections. [Flint, S., The Practitioner 235:56–63 (1991)]. There is currently no wholly satisfactory means of correcting these defects.

Furthermore, there have been efforts to develop and use compositions and methods to correct defects in skin, such as scars and wrinkles, or to augment the tissue of a subject in order to improve the appearance of the skin, particularly facial skin. The principal method employed to correct such defects involves injecting a filler composition into the dermal layer of the skin proximate to the defect or desired tissue augmentation. Examples of non-biological filler compositions used in these roles include mineral oil, paraffin, silicone fluid, autologous fat, gelatin powder mixes, polymethylmethacrylate microspheres, cross-linked polydimethylsiloxane, ""TEFLON"" paste, reconstituted bovine collage, and autologous human collagen.

However, the use of these compositions comprises inherent limitations. For example, the use of mineral oil, paraffin and similar oils and waxes has resulted in complications such as local chronic edema, lymphadenopathy, scarring and ulcerations (Devore et al., *Effectiveness of injectable filler materials for smoothing wrinkle lines and depressed scars.* Medical Progress Through Technology 20:243–250 (1994 which is hereby incorporated by reference in its entirety).

The use of reconstituted bovine collagen to correct defects or augment tissue also possesses inherent limitations. For example, it has been reported that reconstituted bovine collage is only moderately effective, and is associated with infrequent, but controversial, adverse reactions. In addition, it is rapidly broken down and resorbed in vivo, providing only a temporary correction of a skin defect or augmentation. More importantly, reconstituted bovine collagen may elicit an immune response in the subject. Id.

As explained above, gelatin matrix implant such as that sold under the mark "FRIBEL", is a composite material of porcine gelatin powder and o-aminocaproic acid which are dispersed in 0.9% (by volume) sodium chloride solution and an aliquot of the recipient's plasma mixed in a 1:1 ratio, is also used to correct skin defects and augment tissue. However, this material also possess inherent limitations. Specifically gelatin matrix does not appear to have applications in the treatment of wrinkle lines. Moreover, since a large bore needle (27 gauge or greater) is used to inject the gelatin matrix into the subject's skin, treatment with gelatin results in greater discomfort and pain to the subject as opposed to the injection of other fillers. Id.

In addition, the use of autologous fat injections to correct a skin defect or augment tissue in a subject, while eliminating the potential of eliciting an immune response, also possesses disadvantages. More specifically, prior to its injection, fat must be processed by skilled clinicians in aseptic conditions to maintain sterility. In addition, the injections are not dermal but are subcutaneous or subdermal. Also, a very large bore needle (as large as 16 gauge) is needed to inject the fat into a subject, resulting in great pain, moderate bruising, and formation of visible puncture holes. Moreover, fat injections are subject to rapid resorption, and must be repeated in order to maintain skin augmentation or defect correction.

The use of autologous, injectable dermal collagen to correct defects or augment tissue has also met with limited success. For example, if large concentrations of collagen are injected, a 27 gauge needle or larger is used, resulting in the infliction of pain on the subject. Furthermore, serial injections are required in order to compensate for the gradual resorption of autologous collagen.

Hence, what is needed is an efficient non-surgical composition that promotes the regeneration of tissues of the gums or the palate and bone that have degenerated as a result of periodontal disease or trauma.

Moreover, what is needed is a composition and method for promoting regeneration of tissue that does not elicit an immune response in the subject at the site of desired tissue regeneration.

What is also needed is a composition that can be used in non-surgical methods to correct defects in skin, such as scars or wrinkles, and augment tissue in a subject, particularly facial tissue, which is not rapidly resorbed by the body so that additional injections are required.

U.S. Pat. No. 5,591,444, U.S. Pat. No. 5,660,850, and U.S. Pat. No. 5,665,372 are incorporated herein by reference in their entirety.

SUMMARY OF THE INVENTION

The present invention provides a composition for promoting regeneration of tissue in a subject that has degenerated as a result of a disease or disorder, and a method of using the composition that does not suffer from the shortcomings of other methods described above. The present invention is based on the inventors' discovery of the successful use of autologous fibroblasts, with and without various forms of matrix, filler or carrier material, to regenerate tissue in a subject, correct skin defects in the subject, or augment tissue in the subject. Fibroblasts are connective-tissue cells involved in tissue repair. When a tissue is injured, nearby fibroblasts migrate into the wound, proliferate, and produce large amounts of collagenous matrix, which helps to isolate and repair the damaged tissue. [Alberts et al., *Molecular Biology of the Cell*, p. 987, 2nd ed., (1992)].

Broadly, the present invention extends to a method for regenerating a subject's tissue (a) that has degenerated as a result of a disease or disorder or (b) that has a defect, comprising the steps of providing a pharmaceutical composition comprising autologous, passaged fibroblasts, identifying a site of tissue degeneration, and injecting an effective amount of the composition into tissue at the site of tissue degeneration so that the tissue is augmented and regeneration of tissue is promoted.

Injection of a pharmaceutical composition of the present invention can be into tissues of the subject comprising the periodontal pocket and/or the periodontal tissue adjacent to the area of degeneration or into tissue subadjacent to a defect in the oral mucosa, or into the tissue of the palate of a human subject, in order promote regeneration of tissue in the oral mucosa, the gingiva, or the palate. Typical defects in the oral mucosa or palate that can be corrected with this embodiment of the present invention include those caused by trauma, dermatoses, recurrent aphthous stomatitis, and infections, or a disease or disorder. Moreover, the present invention can be used to correct defects in the skin, such as scars, wrinkles, laugh lines, rhytids, stretch marks, depressed scars, cutaneous depressions of non-traumatic origin, acne scarring, or subcutaneous atrophy from acne, trauma, congenital malformation, or aging. Moreover, the invention can be used to treat defects such a hypoplasia of the lips, or labial folds. In addition, the composition can be used to repair a defect, disorder or disease of bone, e.g., bones such as, for example, facial bones including orbits, mandibles, maxillae, zygomatic bones, crania, and nasal bones. Bone diseases, disorders, or defects, include, for example, tooth extraction-related bone defects or those due to periodontal disease.

A disease or disorder which results in tissue degeneration in a subject that can be treated with the present invention includes, but is not limited to, defects of the oral mucosa, periodontal disease, trauma to the oral mucosa (e.g., extraction of a tooth), diabetes, cutaneous ulcers, or venous stasis. Moreover, periodontal disease can include periodontal degeneration, gingivitis, or a non-healing wound of the palatal mucosa or the gingival mucosa.

The present invention further extends to a method of forming a composition comprising autologous, passaged fibroblasts which are substantially free of immunogenic proteins, such as culture medium serum-derived proteins, and are histocompatible with a subject. This method comprises the steps of collecting a biopsy of dermis from a subject, isolating the autologous fibroblasts contained in the biopsy from extracellular matrix and other cells contained in the biopsy, culturing the autologous fibroblasts in a culture medium that permits expansion of the autologous fibroblasts, incubating the autologous fibroblasts in a protein free medium for at least about 2 hours between about 30° C. and about 37.5° C., and exposing the incubated autologous fibroblasts to a proteolytic enzyme so as to suspend the fibroblasts. An example of a culture medium that permits expansion of autologous fibroblasts comprises between 0.0% and about 20% serum, wherein the serum can be either human or non-human. Also, the biopsy from dermis can comprise tissue from the gums, palate or skin of the subject. Hence autologous fibroblasts from the gums, plate or skin have applications in the present invention.

In another embodiment, the passaged autologous fibroblasts can be added to a pharmaceutically acceptable carrier to form a pharmaceutical composition. In producing a pharmaceutical composition of the present invention, immunogenic proteins, e.g., culture medium serum-derived proteins, are removed from the autologous fibroblasts, thereby avoiding an immunological reaction in a subject when such cells are reintroduced to the subject proximate to the site of tissue degeneration or defect.

In addition, the present invention extends to a device for delivering a pharmaceutical composition of the present invention to a site proximate to the site of tissue degeneration or defect in a subject, wherein the device comprises a hypodermic syringe having a syringe chamber, a piston disposed therein, an orifice communicating with the chamber, a pharmaceutical composition comprising autologous passaged fibroblasts and a pharmaceutically acceptable carrier, such that the pharmaceutical composition is disposed in the chamber, and a hypodermic needle is fixed to the orifice.

Tissues which have suffered degeneration or have a defect that can be treated with a device of the present invention include the oral mucosa, the gingival mucosa, and the palatal mucosa. Moreover, diseases or disorders which can be treated with this device include periodontal degeneration, gingivitis, or a non-healing wound of the palatal mucosa or the gingival mucosa. Other defects that can be treated with this invention include those listed above.

The present invention further extends to a composition for repairing tissue that has degenerated in a subject as result of a disease, disorder or defect in the subject, wherein the composition comprises a biodegradable acellular matrix, and autologous passaged fibroblasts (derived, for example, from the gums, palate, or skin of the subject) and is substantially free of immunogenic proteins, e.g., culture medium xenogeneic (e.g., fetal bovine) serum-derived proteins, wherein the autologous fibroblasts are integrated into the biocompatible biodegradable acellular matrix. In an embodiment of the present invention, the biocompatible biodegradable acellular matrix comprises exogenous proteins, such as any type of collagen. In addition, the biodegradable acellular matrix can be comprised of any type of collagen and glycosaminoglycans (GAG) cross-linked with, for example, glutaraldehyde, or any type of collagen.

In yet another example, the biodegradable acellular matrix comprises one or more of gelatin, polyglycolic acid, cat gut, demineralized bone, or hydroxyapatite. Other appropriate matrices consist of bone from which substantially all (e.g., at least 80%, at least 90%, at least 95%, at least 99%, or even 100% by weight) organic material has been removed (referred to herein as "anorganic bone"); such matrices can, optionally, include exogenous collagen in various amounts (e.g., about 1%, about 2%, about 5%, about 10%, or about 20% by dry weight).

Also, diseases, disorders or defects resulting in degeneration of tissue in a subject which can be treated with the present invention, comprise defects of the oral mucosa, trauma (e.g., extraction of a tooth) to the oral mucosa or oral bones such as the maxillary or mandibular bones, periodontal disease, diabetes, cutaneous ulcers, or venous stasis. In addition, examples of periodontal disease which result in tissue degeneration include, but are not limited to, periodontal degeneration, gingivitis, or non-healing wounds of the palatal mucosa or gingival mucosa, or bone degeneration. Other defects that can be treated with this invention include skin defects, such as scars, wrinkles, laugh lines, stretch marks, depressed scars, cutaneous depressions of non-traumatic origin, acne scarring, or subcutaneous atrophy from acne, trauma, congenital malformation, or aging. Moreover, the invention can be used to treat defects such a hypoplasia of the lips, labial folds, or bone defects, e.g., defects of bones such as, for example, facial bones including orbits, mandibles, maxillae, zygomatic bones, crania, and nasal bones.

Also encompassed by the invention is a method for making a composition for the repair of tissue that has degenerated in a subject as result of a disease, disorder, or defect in the subject. The method comprises: providing a suspension of autologous, passaged fibroblasts; providing a biodegradable acellular matrix; incubating the suspension of autologous passaged fibroblasts with the biodegradable acellular matrix such that the autologous passaged fibroblasts integrate within the biodegradable acellular matrix; and removing substantially all culture medium serum-derived proteins from said biodegradable acellular matrix and said integrated fibroblasts to form a composition for promoting the repair of tissue. Sufficient autologous, passaged fibroblasts integrate within the biodegradable acellular matrix to substantially fill the space on and within the biodegradable acellular matrix available for cells. As used herein, "substantially" fill with passaged autologous fibroblasts means to fill to a level sufficient to prevent an amount of cell proliferation that degrades a collagen matrix to a practically deleterious level, as a person skilled in the art can readily determine for a particular embodiment.

The biodegradable acellular matrix used in this method can contain exogenous protein such as, for example, any type of collagen, e.g., any type of collagen and glycosaminoglycans, cross-linked with, for example, glutaraldehyde. The biodegradable acellular matrix can contain one or more of the following substances: gelatin, polyglycolic acid, cat gut, demineralized bone, hydroxyapatite, gelatin, polyglycolic acid, cat gut, or anorganic bone with or without any of range of concentrations of exogenous collagen (see below).

The disease, disorder, or defect to be treated can be a defect of an oral mucosa, trauma to an oral mucosa, periodontal disease, diabetes, a cutaneous ulcer, venous stasis, a scar of skin, or a wrinkle of skin. Alternatively, the disease or disorder can be periodontal disease, and the periodontal disease can be periodontal degeneration, gingivitis, or a non-healing wound of a palatal mucosa or a gingival mucosa.

In this method the step of providing a suspension of autologous, passaged fibroblasts can involve: collecting a biopsy of dermis or palate of the subject; separating dermal autologous fibroblasts from the biopsy; culturing the dermal autologous fibroblasts in a culture medium containing (a) between 0.0% and about 20% human or non-human serum and (b) a reagent that prevents the growth of mycoplasma; and exposing the incubated dermal autologous fibroblasts to a proteolytic enzyme so as to suspend fibroblasts. The step of collecting a biopsy of dermis can involve collecting a biopsy from gums, palate or skin of the subject. The reagent can contain tylosin and, optionally, one or more of the following compounds: gentamicin, ciprofloxacine, alatrofloxacine, azithromycin, or tetracycline.

The present invention further extends to a method of using a composition for promoting regeneration of tissue, wherein the method comprises providing passaged autologous fibroblasts integrated into a biodegradable acellular matrix, identifying a site (i) of tissue degeneration due to a disease or disorder in the subject or (ii) a defect in the tissue of the subject, and placing the composition on the site so that the tissue is repaired. Autologous passaged fibroblasts used herein can comprise fibroblasts from the gums, palate or skin of the subject.

Diseases, disorders, or defects which can be treated with this method include, but are not limited to, defects of the oral mucosa, trauma to the oral mucosa (e.g., extraction of a tooth), periodontal disease, diabetes, cutaneous ulcers, or venous stasis. Examples of periodontal disease that can be treated with the present invention comprise periodontal degeneration, gingivitis, or a non-healing wound of the palatal mucosa or the gingival mucosa. Moreover, defects (e.g., skin defects such as scars or wrinkles) can be treated with the composition of the present invention. In a preferred embodiment, such defects are treated with a composition comprising fibroblasts from the palate. Any of the above listed diseases, disorders, or defects can also be treated by these methods.

Furthermore, biodegradable acellular matrices having applications in the present invention may comprise exogenous proteins. Examples of such matrices include matrices comprising any type of collagen, or any type of collagen and glycosaminoglycans (GAG) cross-linked with, for example, glutaraldehyde.

Other examples of biodegradable acellular matrices having applications in the present invention include one or more of gelatin, polyglycolic acid, cat gut, demineralized bone (e.g., demineralized human bone), or hydroxyapatite. Other appropriate matrices consist of bone from which substantially all (e.g., at least 80%, at least 90%, at least 95%, at least 99%, or even 100% by weight) organic material has been removed (referred to herein as "anorganic bone"); such matrices can, optionally, include exogenous collagen, in various amounts (e.g., about 1%, about 2%, about 5%, about 10%, or about 20% by dry weight).

The present invention further extends to an injectable composition for correcting a defect in skin of a subject, or augmenting tissue of a subject, said injectable composition comprising passaged, autologous fibroblasts substantially free of immunogenic proteins, e.g., culture medium serum-derived proteins, and a biodegradable, acellular injectable filler material. Passaged autologous fibroblasts having applications in an injectable composition of the present invention are from gums, palate or skin of the subject.

Furthermore, the present invention extends to an injectable composition as described above, wherein the biodegradable, acellular injectable filler material comprises endogenous proteins. In particular, the acellular injectable filler material of an injectable composition of the present invention comprises an injectable dispersion of autologous collagen fibers having a concentration in the composition of at least 24 mg/ml of composition.

In addition, the present invention extends to an injectable composition as described above, wherein the biodegradable acellular injectable filler material comprises exogenous proteins, such as any type of collagen. An example of an exogenous collagen having applications in an injectable composition of the present invention is reconstituted bovine collagen fibers cross-linked with glutaraldehyde.

Furthermore, the filler material can comprise any type of solubilized gelatin either alone, or in combination with other materials. In a particular example, the filler material comprises porcine gelatin powder and o-aminocaproic acid dispersed in sodium chloride solution and an aliquot of plasma from the subject to be injected with the composition. Preferably the ratio of sodium chloride to serum is 1:1 by volume. Other examples of materials having applications in the present invention as biodegradable, acellular injectable filler material include, but are not limited to polyglycolic acid or cat gut.

The present invention further extends to a method for correcting a defect in skin of a subject, or augmenting tissue of a subject, wherein the method comprises injecting an effective amount of an injectable composition comprising autologous passaged fibroblasts substantially free of immunogenic proteins (e.g., culture medium serum-derived proteins) and a biodegradable, acellular injectable filler material, into the skin of the subject at the site of the skin defect or desired tissue augmentation, so that regeneration of tissue at the site is promoted at the site.

Moreover, the present invention extends to a method for correcting a defect in skin of a subject, or augmenting tissue of a subject, the method comprising the steps of injecting autologous fibroblasts substantially free of immunogenic proteins, e.g., culture medium serum-derived proteins, into the subject at a site of a skin defect or desired tissue augmentation, and subsequently injecting a biodegradable, acellular injectable filler material into the site. In a particular embodiment of this method of the present invention, the duration between injecting the autologous fibroblasts into the subject and injecting the biodegradable acellular injectable filler into the subject is about two weeks.

Autologous fibroblasts having applications in methods of the present invention for correcting a defect in skin of a subject, or augmenting tissue of a subject can be obtained from the gums, palate of skin of the subject.

The present invention further extends to a method for correcting a defect in skin of a subject, or augmenting tissue of the subject, as described above, wherein the biodegradable, acellular injectable filler material comprises endogenous proteins. For example, the biodegradable acellular injectable filler material can comprise an injectable dispersion of autologous collagen fibers, preferably at a concentration of at least 24 mg of autologous fibers per ml of composition.

Furthermore, the present invention extends to a method for correcting a defect in skin or other tissues of a subject (such as those described above), or augmenting tissue of the subject, also as described above, wherein the biodegradable, acellular filler material of the composition comprises exogenous proteins such as, for example, any type of collagen. An example of collagen having applications in a method of the present invention comprises reconstituted bovine collagen fibers cross-linked with, for example, glutaraldehyde.

Other examples of biodegradable, acellular injectable filler material for use in a method for correcting a defect in skin or a subject, or augmenting tissue of the subject include, but are not limited to solubilized gelatin, polyglycolic acid, or cat gut sutures. More specifically, an example of acellular injectable filler material having applications in the present invention comprises porcine gelatin powder and aminocaproic acid dispersed in sodium chloride solution, and an aliquot of plasma from the subject. Preferably, the ratio of sodium chloride solution to the aliquot of serum is 1:1 by volume. Furthermore, the sodium chloride solution comprises 0.9% sodium chloride by volume.

In addition, the present invention extends to a method for correcting a defect in skin of a subject, or augmenting tissue of a subject, as described above, wherein the ratio of autologous fibroblasts substantially free of immunogenic proteins (e.g., culture medium serum-derived proteins) biodegradable, acellular injectable filler material is approximately 1:1 by volume.

Accordingly, it is an object of the present invention to provide a composition for augmenting tissue, or promoting regeneration of tissue such as the oral mucosa, the gingival mucosa, or the palatal mucosa or skin, which has degenerated as a result of a disease or disorder. Examples of such disorders include periodontal disease, trauma, dermatoses, recurrent aphthous stomatitis, infections, scars, or wrinkles and the others listed above.

It is another object of the present invention to provide a composition for augmenting tissue, or promoting regeneration of tissue, wherein the composition is histocompatible with a subject, thereby avoiding elicitation of an immune response and inflammation in the tissues of the subject near the site of degeneration of tissue.

It is yet another object of the present invention to provide method of promoting tissue regeneration that does not require surgery.

It is yet still another object of the present invention to promote regeneration of tissue in a subject without the use of antibiotics in the subject, and hence prevent the emergence of antibiotic resistant pathogens and deleterious side effects associated with antibiotics in the subject.

It is another object to provide an injectable composition for correcting defects in skin, such as scars or wrinkles, or for augmenting tissue in a subject, particularly facial tissue (such as lips), which includes passaged autologous fibroblasts that can withstand resorption so that subsequent injections are not needed, and to prevent the elicitation of an immune response in the subject.

It is yet another object of the present invention to provide methods for correcting defects in skin, such as scars or wrinkles, or for augmenting tissue in a subject, that employs the injectable composition set forth above, that inflicts limited pain on the subject, and does not elicit an immune response in the subject, and is not rapidly resorbed.

Other objects and advantages will become apparent to those skilled in the art from a review of the ensuing description.

DETAILED DESCRIPTION OF THE INVENTION

The present invention is based, in part, on the recognition that living cells normally present in tissue that has degenerated, particularly fibroblasts, are the ideal material to augment the volume of tissue in order to promote regeneration of tissue. Hence the present invention ameliorates and reverses the degenerative effects of a disease or disorder which results in tissue degeneration.

Additionally, the present invention is based on the recognition that an ideal composition with which to augment the oral mucosa subadjacent to a defect, to treat defects in the palate or gingiva, or to promote regeneration of tissue that has degenerated as a result of periodontal disease, would comprise living cells normally present in such tissues, particularly fibroblasts.

Moreover, the present invention is based on the recognition that an abundant supply of autologous cells of the desired type can be obtained by culturing a biopsy specimen taken from the skin, palate or gums of a subject several weeks prior to treating the tissue degenerating disease, disorder, or defect. The invention is further based on the recognition that, after such a tissue culture expansion, the autologous cells will contain a significant quantity of immunogenic proteins, e.g., proteins derived from xenogeneic (e.g., bovine, horse, goat, or sheep) serum used to supplement the medium used for tissue culture, but that the immunogenic proteins can be removed, prior to treatment of the subject.

The term "biodegradable" as used herein denotes a composition that is not biologically harmful and can be chemically degraded or decomposed by natural effectors (e.g., weather, soil bacteria, plants, animals).

The term "autologous" as used herein refers to cells removed from a donor and administered to a recipient, wherein the donor and recipient are the same individual.

The term "effective amount" as used herein refers to the injection of an amount of pharmaceutical composition of the present invention to promote tissue regeneration in of tissue that has degenerated in a subject.

As used herein, a composition or cells (e.g., autologous passaged fibroblasts) that are "substantially free of culture medium serum-derived proteins" are a composition or cells in which the fluid surrounding the composition or cells or incorporated into the body of biodegradable acellular matrices that are components of such compositions contains less than 0.1% (e.g., less than 0.02, 0.04, 0.008, or 0.0016%) of the xenogeneic serum contained in the tissue culture medium in which the composition or cells were last cultured.

EXAMPLE I

Administration of a Suspension of Autologous Fibroblasts to Promote Tissue Regeneration and Correct Defects in Tissues Method of Obtaining an Injectable Cell Pharmaceutical Composition As disclosed above, one embodiment of the present invention comprises a method for regenerating tissue that has been damaged in a subject as a result of a disease or disorder in the subject, wherein the method comprises providing a pharmaceutical composition comprising of autologous, passaged fibroblasts substantially free of immunogenic proteins (e.g., culture medium serum-derived proteins), identifying a site of tissue degeneration or a defect in tissue, injecting an effective amount of the pharmaceutical composition into the tissue at the site of the tissue degeneration or defect so that the tissue is augmented, and the growth of tissue is promoted at the site of degenerated tissue.

A disease or disorder which promotes tissue degeneration in a subject, and can be treated with this aspect of the present invention includes, but is not limited to, defects of the oral mucosa, trauma to the oral mucosa, periodontal disease, diabetes, cutaneous ulcers, or venous stasis. Furthermore, examples of periodontal disease which can be treated with this aspect of the present invention include periodontal degeneration, gingivitis, or a non-healing wound of the palatal mucosa or the gingival mucosa. In addition, defects in skin and other tissues (see above) can be treated with the present invention.

The invention can be practiced by injecting any undifferentiated mesenchymal cell that can be expanded in culture. In a preferred embodiment, dermal fibroblasts are injected because they can be readily obtained and expanded, and because they are a cell type normally present beneath the gingival mucosa or palatal mucosa. Fibroblasts taken from a biopsy of the gums, palate, or skin of the subject can be used in the present invention.

In providing a composition of the present invention, a dermal fibroblast culture is initiated from a 1 to 5 mm full thickness biopsy specimen of the gums, palate or skin of a subject suffering from tissue degeneration. Because of the phenomenon of allograft rejection, which is well known to transplantation surgeons and immunologists, it is essential that the cultured fibroblasts be histocompatible with the host. Histocompatibility can be ensured by obtaining a biopsy of the subject to be treated and culturing the fibroblasts from this specimen.

Before the initiation of the culture, the biopsy is washed repeatedly with antibiotic and antifungal agents. An exemplary "wash medium" can contain tissue culture medium such as Dulbecco's Modified Eagle's Medium (DMEM) and all or some of the following antibiotics: gentamicin, amphotericin B (Fungizone), and tylosin (manufactured by Gibco-BRL and sold by Life Technologies, Rockville, Md., as "Anti-PPLO", PPLO being an acronym for "pleuropneumonia-like organism", now known as "mycoplasma"). Gentamicin can be used at a concentration of 0.1–5.0 (e.g., about 0.5) mg/ml. Amphotericin B can be used at a concentration of 0.0005–0.0125 (e.g., about 0.0025) mg/ml. Tylosin can be used at a concentration of 0.012–1.2 (e.g., 0.12) mg/ml. The specimen of dermis is then separated into small pieces. The pieces of the specimen are individually placed onto the dry surface of a tissue culture flask and allowed to attach for between about 5 and about 10 minutes, before a small amount of medium is slowly added, taking care not to displace the attached tissue fragments. After about 48 hours of incubation, the flask is fed with additional medium. When a T-25 flask is used to start the culture, the initial amount of medium is about 1.5–2.0 ml. The establishment of a cell line from the biopsy specimen ordinarily takes between about 2 and 3 weeks, at which time the cells can be removed from the initial culture vessel for expansion.

During the early stages of the culture, it is desirable that the tissue fragments remain attached to the culture vessel bottom; fragments that detach should be reimplanted into new vessels. The fibroblasts can be stimulated to grow by a brief exposure to EDTA-trypsin, according to techniques well known to those skilled in the art. The exposure to trypsin is too brief to release the fibroblasts from their attachment to the culture vessel wall. Immediately after the cultures have become established and are approaching confluence, samples of the fibroblasts can be processed for frozen storage, such as in liquid nitrogen. Presently, numerous methods for successfully freezing cells for later use are known in the art, and are included in the present invention. The frozen storage of early rather than late passage fibroblasts is preferred because the number of passages in cell culture of normal human fibroblasts is limited.

The fibroblasts can be frozen in any freezing medium suitable for preserving fibroblasts. A medium consisting of about 70% (v/v) growth medium, about 20% (v/v) fetal bovine serum and about 10% (v/v) dimethylsulfoxide (DMSO) can be used with good effect. DMSO can also be substituted with, for example, glycerol. Thawed cells can be used to initiate secondary cultures to obtain suspensions for use in the same subject without the inconvenience of obtaining a second specimen.

Any tissue culture technique that is suitable for the propagation of dermal fibroblasts from biopsy specimens may be used to expand the cells to practice the invention.

Techniques well known to those skilled in the art can be found in R. I. Freshney, Ed., ANIMAL CELL CULTURE: A PRACTICAL APPROACH (IRL Press, Oxford, England, 1986) and R. I. Freshney, Ed., CULTURE OF ANIMAL CELLS: A MANUAL OF BASIC TECHNIQUES, Alan R. Liss & Co., New York, 1987), which are hereby incorporated by reference.

The medium can be any medium suited for the growth of primary fibroblast cultures. The medium can be supplemented with human or non-human serum in an amount of between about 0.0% and about 20% (v/v) to promote growth of the fibroblasts. Higher concentrations of serum promote faster growth of the fibroblasts. An example of medium having application herein comprises glucose DMEM supplemented with about 2 mM glutamine, about 10 mg/L sodium pyruvate, about 10% (v/v) fetal bovine serum and antibiotics ("complete medium"), wherein the concentration of glucose ranges from about 1,000 milligrams per liter of medium to about 4,500 milligrams per liter of medium. Fibroblasts can also be expanded in serum-free medium. Tissue culture growth medium used for culturing the fibroblasts is generally supplemented with antibiotics to prevent microbial (e.g., bacterial, fungal, yeast, and mycoplasma) contamination of the cultures. Mycoplasma contamination is a frequent and particularly vexatious problem in tissue culture. In order to prevent or minimize mycoplasma contamination, an agent such as tylosin can be added to the relevant culture medium. The medium can be further supplemented with one or more (e.g., all) the following antibiotics: gentamicin, ciprofloxacine, alatrofloxacine, azithromycin, and tetracycline. Tylosin can be used at a concentration of 0.006–0.6 mg/ml (e.g., about 0.06) mg/ml. Gentamicin can be used at a concentration of 0.02–0.5 (e.g., about 0.1) mg/ml. Ciprofloxacine can be used at concentration of 0.002–0.05 (e.g., about 0.01) mg/ml. Alatrofloxacine can be used at a concentration of 0.2–5.0 (e.g., about 1.0) $\mu$g/ml. Azithromycin can be used at a concentration of 0.002–0.05 (e.g., 0.01) mg/ml. Tetracycline can be used at a concentration of 0.004–0.1 (e.g., about 0.02) mg/ml. The antibiotics can be present for the whole period of the culture or for only part of the culture period.

Mycoplasmal contamination was tested for by an agar culture method using a culture system such as, for example, a kit marketed by Sigma, St. Louis, Mo., as "Mycoplasma Test Medium" (Cat. No. M 1914) and by PCR. PCR testing was performed by the both the ATCC (Manassas, Va.) and Esoterics Co., Houston, Tex. The ATCC markets a PCR mycoplasma test kit ("Mycoplasma Detection Kit"; cat. no. 90-100K). Using both the agar culture method and the PCR test, a low level of mycoplasmal contamination was detected in four out of fifteen cultures performed in medium supplemented with gentamicin as the only antibiotic; on the other hand, no mycoplasmal contamination was detected in any of 12 cultures containing tylosin (0.06 mg/ml), gentamicin (0.1 mg/ml), ciprofloxacine (0.01 mg/ml), alatrofloxacine (1.0 $\mu$g/ml), azithromycin (0.01 mg/ml), and tetracycline (0.02 mg/ml). The antibiotic mixture was present in the fibroblast cultures only for the first two weeks after initiation. After two weeks of culture antibiotic containing medium was replaced with antibiotic-free medium. Once sufficient cells had grown, they were tested for mycoplasmal as well as bacterial and fungal contamination. Only cells with no detectable contamination were used in the described treatment methods of the invention. Another agent that has been found by the inventors to be useful in preventing mycoplasmal contamination is a derivative of 4-oxo-quinoline-3-carboxylic acid (OQCA) which is sold as Mycoplasma Removal Agent (MRA) by ICN Pharmaceuticals, Inc. (Costa Mesa, Calif.) and was used according to the manufacturer's instructions. This derivative of OQCA can be used at a concentration of 0.1–2.5 (e.g., 0.5) $\mu$g/ml.

Autologous fibroblasts can be passaged into new flasks by trypsinization. For expansion, individual flasks are split 1:3. Triple bottom, T-150 flasks, having a total culture area of 450 cm$^2$, are suitable for the practice of the invention. A triple bottom T-150 flask can be seeded with about 1×10$^6$ to about 3×10$^6$ cells and has a capacity to yield about 8×10$^6$ to about 1.0×10$^7$ cells. When the capacity of the flask is reached, which typically requires about 5–7 days of culture, the growth medium is replaced by serum-free medium; thereafter the cells are incubated, i.e., held at between bout 30° C. and about 37.5° C., for at least 4 hours (e.g., overnight or about 18 hours). The incubation of the cells in serum free medium substantially removes from the cells proteins that are derived from the fetal bovine serum which, if present, can elicit an untoward immune response in the subject. In a preferred embodiment, serum-free medium comprises glucose DMEM supplemented with about 2 mM glutamine, and about 110 mg/L sodium pyruvate, wherein the concentration of glucose can range from approximately 1,000 mg/L of medium to about 4,500 mg/L of medium. In a preferred embodiment, the concentration of glucose is approximately 4,500 mg/L of medium. The serum-free medium can also contain the above-described antibiotics.

At the end of the incubation in serum free medium, the cells are removed from the tissue culture flask by trypsin-EDTA; washed extensively by centrifugation and resuspension; and suspended for injection in an equal volume of injectable isotonic solution with an appropriate physiological osmolarity, which is substantially pyrogen and foreign protein free. An example of such an isotonic solution is isotonic saline. Five triple bottom T-150 flasks, grown to capacity, yield about 3.5×10$^7$ to about 7×10$^7$ cells which are sufficient to make up about 1.2 to about 1.4 ml of suspension. A pharmaceutically acceptable carrier can then be added to the passaged autologous fibroblasts forming a pharmaceutical composition. The phrase "pharmaceutically acceptable" refers to molecular entities and compositions that are not deleterious to the cells, are physiologically tolerable, and do not typically produce an allergic or similar untoward reaction, such as gastric upset, dizziness and the like, when administered to a human. Such compositions include diluents of various buffer content (e.g., Tris-HCl, acetate, phosphate), pH and ionic strength.

Alternatively, the cells can be transported on ice at about 4° C. so long as they are injected within 24–48 hours of the time that the pharmaceutical composition is made. The cells can be suspended in an appropriate physiological solution with appropriate osmolarity and tested for pyrogen and endotoxin levels, except for the absence of phenol red pH indicator, and the replacement of the fetal bovine serum by the subject's serum for such transportation (transport medium). In another embodiment the cells can be suspended in Krebs-Ringer solution comprising 5% dextrose or any other physiological solution. The cells can be aspirated and injected in the transport medium.

The volume of saline or transport medium in which the cells are suspended is related to such factors as the number of fibroblasts the practitioner desires to inject, the extent of the damage due to tissue degeneration or defect, or the size, the number of the defects that are to be treated, and the urgency of the subject's desire to obtain the results of treatment. Moreover, the practitioner can suspend the cells in a larger volume of medium and inject correspondingly fewer cells at each injection site.

Device for Treating Degenerated Tissue with
Autologous Passaged Fibroblast Pharmaceutical
Composition of the Present Invention As explained above, the present invention extends to a device delivering a pharmaceutical composition of autologous passaged cells described above, to a point proximate to the site of tissue degeneration, or defects of the palate, oral mucosa or skin. Such a device comprises a hypodermic syringe having a syringe chamber, a piston disposed therein, an orifice communicating with the chamber, a pharmaceutical composition comprising autologous, passaged fibroblasts, and a pharmaceutically acceptable carrier thereof, such that the pharmaceutical composition is disposed in the chamber, and a hypodermic needle is fixed to the orifice.

The Administration of a Pharmaceutical
Composition

A pharmaceutical composition of the invention can be used to treat tissue degeneration in a subject as a result of a disorder or disease, such as periodontal disease, or defects of the oral mucosa or skin, such as scars or wrinkles, by use of the following techniques.

Initially, the tissue to be injected is prepped with alcohol and stretched to give a taut surface. If the tissue degeneration is the result of periodontal disease, the tissue to be injected is periodontal tissue, including periodontal pockets. If the tissue to be injected contains defects in the palate or gums of the subject, the tissue to be injected with a pharmaceutical composition of the present invention is subadjacent to the defect. Also, if the tissue to be injected is the skin, in order to treat defects, e.g., scars, wrinkles, or any of the defects listed above, it is also injected into the dermis or subcutaneous tissue.

After the tissue to be injected has been prepped, a syringe is filled with a pharmaceutical composition of the present invention and fitted with a 30 gauge needle. The needle is inserted into the tissue as superficially as possible, and the orientation of the bevel is not critical to the success of this method of the present invention. The injection of the pharmaceutical composition is made by gentle pressure until a slight blanch is seen in the injected tissue. Multiple serial injections are made.

EXAMPLE II

A Composition for Promoting the Regeneration of
Tissue that has Degenerated in a Subject Also disclosed in the present invention is a composition for promoting the regeneration of tissue that degenerated in a subject. Such degeneration can occur as a result of periodontal disease, trauma, dermatoses, recurrent aphthous stomatitis, or infections to name only a few. Other relevant diseases and disorders are listed above. Moreover, examples of periodontal disease which can cause tissue degeneration include periodontal degeneration, gingivitis, or non-healing wounds of the palatal mucosa or gingival mucosa. Moreover, a composition of the present invention can also be used to correct defects in tissue of a subject, such as, for example, defects in the palatal mucosa, gingival mucosa, or defects in skin, e.g., any of those described above. Such compositions can be used, for example, for healing extraction sockets after extraction of a tooth. Moreover, they can be used to fill extraction-associated bone defects and to rebuild bone in periodontal disease. They can be used, for example, to repair dental ridges and mandibular bone, maxillary bone, and sinus floor defects. Indeed they can be used to repair any bony defect in the body, including, for example, non-union of fractured bones such as long bones. A composition of the present invention comprises a biodegradable acellular matrix, and autologous passaged fibroblasts substantially free of immunogenic proteins (e.g., culture medium serum-derived proteins), wherein the autologous fibroblasts are integrated into the biodegradable acellular matrix.

Moreover, disclosed herein is a method of making a composition of the present invention to promote regeneration of tissue in a subject. Such a method comprises providing a suspension of passaged autologous fibroblasts substantially free of immunogenic proteins, e.g., culture medium serum-derived proteins, providing a biodegradable acellular matrix, incubating the biodegradable acellular matrix with the suspension of passaged autologous fibroblasts such that the autologous fibroblasts integrate within the biodegradable acellular matrix forming a composition for promoting regeneration of tissue. Also disclosed herein is a method of using a composition of the present invention, comprising identifying a site of tissue degeneration, and applying the composition for promoting regeneration of tissue to the site of tissue degeneration.

In order to produce a composition of the present invention, autologous passaged fibroblasts substantially free of immunogenic proteins (e.g., culture medium serum-derived proteins) must be made available to avoid the phenomenon of allograft rejection, which is well known to transplantation surgeons and immunologists. Hence, it is essential that the cultured fibroblasts be histocompatible with the host. Histocompatibility can be ensured by obtaining a biopsy of the gums, palate or skin of the subject to be treated, and culturing the fibroblasts from this specimen.

Before the initiation of the dermal fibroblast culture, a biopsy of 1–3 mm is taken from the gums, palate or skin of the subject, and washed repeatedly with antibiotic and antifungal agents (see above). The specimen of dermis is then separated into small pieces. The pieces of the specimen are individually placed onto a dry surface of a tissue culture flask and allowed to attach for between 5 and 10 minutes before a small amount of medium is slowly added, taking care not to displace the attached tissue fragments. After 48 hours of incubation, the flask is fed with additional medium. When a T-25 flask is used to start the culture, the initial amount of medium is 1.5–2.0 ml. The establishment of a cell line from the biopsy specimen ordinarily takes between 2 and 3 weeks, at which time the cells can be removed from the initial culture vessel for expansion.

During the early stages of the culture it is desirable that the tissue fragments remain attached to the culture vessel bottom; fragments that detach should be reimplanted into new vessels. The autologous fibroblasts can be stimulated to grow by a brief exposure to trypsin-EDTA, according to techniques known to those skilled in the art. The exposure to trypsin is too brief to release the fibroblasts form their attachment to the culture vessel wall.

Immediately after the cultures have become established and are approaching confluence, samples of the autologous fibroblasts can be processed for frozen storage in, for example, liquid nitrogen. The frozen storage of early rather than late passage fibroblasts is preferred because the number of passages in cell culture of normal human fibroblasts is limited.

The autologous fibroblasts can be frozen in any freezing medium suitable for preserving cells. A medium consisting of about 70% growth medium, about 20% (v/v) fetal bovine serum and about 10% (v/v) dimethylsulfoxide (DMSO) can be used with good effect. DMSO can also be substituted with, for example, glycerol. Thawed cells can be used to initiate secondary cultures to obtain suspensions for use in the same subject without the inconvenience of obtaining a second specimen.

Any tissue culture technique that is suitable for the propagation of dermal fibroblasts from biopsy specimens may be used to expand the cells to practice the invention. Techniques for propagation known to those skilled in the art can be found in R. I. Freshney, Ed., ANIMAL CELL CULTURE: A PRACTICAL APPROACH (IRL Press, Oxford England, 1986) and R. I. Freshney, Ed., CULTURE OF ANIMAL CELLS: A MANUAL OF BASIC TECHNIQUES, Alan R. Liss & Co., New York, 1987), which are hereby incorporated by reference.

The medium can be any medium suited for the growth of primary autologous fibroblast cultures. In most instances, the medium is supplemented with human or non-human serum in the amount of between about 0.0% and about 20% (v/v) to promote growth of the autologous fibroblasts. Higher concentrations of serum promote faster growth of the fibroblasts. In a preferred embodiment the serum is fetal bovine serum, which is added to a final concentration of about 10% of medium. Moreover, the medium can be glucose DMEM supplemented with about 2 mM glutamine, about 110 mg/L sodium pyruvate, about 10% (v/v) fetal bovine serum and antibiotics ("complete medium"), wherein the concentration of glucose ranges from approximately 1,000 mg/L of medium to approximately 4,500 mg/L of medium. Preferably, the concentration of glucose in the medium is approximately 4,500 mg/L of medium. The medium will generally also contain antibiotics such those described above.

Autologous fibroblasts can be passaged into new flasks by trypsinization. For expansion, individual flasks are split 1:3. Triple bottom, T-150 flasks, having a total culture area of 450 cm$^2$, are suitable for the practice of the invention. A triple bottom T-150 flask can be seeded with about 1×10$^6$ to about 3×10$^6$ to about 3×10$^6$ cells and has a capacity to yield about 8×10$^6$ to about 1.0×10$^7$ cells. When the capacity of the flask is reached, which typically requires 5–7 days of culture, the growth medium is replaced by serum-free medium; thereafter the cells are incubated, i.e., held at between about 30° C. and about 37.5° C., for at least 4 hours (e.g., overnight, or about 18 hours). The incubation of the cells in serum free medium substantially removes from the cells proteins that are derived from the fetal bovine serum which, if present, would elicit an immune subject. In a preferred embodiment, the serum-free medium comprises glucose and DMEM supplemented with about 2 mM glutamine, about 110 mg/L sodium pyruvate, wherein the concentration of glucose ranges from approximately 1,000 mg/L of medium to approximately 4,500 mg/L of medium, and preferably is 4,500 mg/L of medium.

A biodegradable acellular matrix is then provided. Examples of such matrices which can be used in the present invention include, but are not limited to, acellular matrices comprising exogenous proteins, or matrices comprising biodegradable polymers.

Numerous biodegradable acellular matrices comprising exogenous proteins are presently available, and have ready applications in the present invention. An embodiment of such biodegradable acellular matrices are matrices comprising any type of collagen, or any type of collagen with glycosaminoglycans (GAG) cross-linked with, for example, glutaraldehyde. Examples of collagen matrices having application in the present invention are absorbable collagen sponges made by the Calcitek Company of Carlsbad, Calif. These collagen sponge dressings, sold under the names "COLLATAPE®," "COLLACOTE®," and "COLLA-PLUG®" are made from cross-linked collagen extracted from bovine deep flexor (Achilles) tendon, and glycosaminoglycans (GAGS). These products are soft, pliable, nonfriable, and non-pyrogenic. In addition, more than 90% of this product consists of open pores. An alternative biodegradable acellular matrix can consist of collagen (e.g., bovine porcine collagen type I) formed into a thin membrane. Such a membrane is manufactured by the Calcitek Company and is marketed as BioMend™. Another such membranous matrix manufactured by ED. GEISTLICH SÖHNE AG of Wolhusen, Switzerland, is made of porcine type I and type III collagen and is marketed as Bio-Gide®. Bio-Gide® has a bilayer structure with one surface that is porous allowing the ingrowth of cells and a second surface that is dense and will prevent the ingrowth of fibrous tissue. Another biodegradable acellular matrix can be made from bone spongiosa formed into granules or blocks. This material consists of animal (e.g., human, non-human primate, bovine, sheep, pig, or goat) bone from which substantially all organic material (e.g., proteins, lipids, nucleic acids, carbohydrates, and small organic molecules such as vitamins and non-protein hormones) have been removed. This type of matrix is referred to herein as an anorganic matrix. One such matrix, which is marketed as either Bio-Oss® spongiosa granules or Bio-Oss® blocks, is manufactured by ED. GEISTLICH SÖHNE AG. This company also manufactures a block-type matrix (Bio-Oss® collagen), also consisting of the anorganic bone, but containing in addition approximately 10% by weight of collagen fibers. Other biodegradable acellular matrices having applications in the present invention can contain one or more of gelatin, polyglycolic acid, or cat gut sutures, demineralized bone, hydroxyapatite, or mixtures of these substances. For example, a matrix made from demineralized human bone and formed into small blocks is marketed as Dynagraft™ matrix by GenSci Regeneration Laboratories, Inc. Demineralized bone can be combined, for example, with collagen to produce a matrix in the form of a sponge, block, or membrane. Synthetic polymers made from one or more monomers can also be used to make the biodegradable acellular matrices of the invention. The matrices can be made from one or more of such synthetic polymers. The synthetic polymers can also be combined with any of the above-mentioned substances to form matrices. Different polymers forming a single matrix can be in separate compartments or layers. For example, Gore-Tex, Inc. manufactures a porous biodegradable acellular matrix (GORE RESOLUT XT Regenerative Material) that is composed of a synthetic bioabsorbable glycolide and trimethylene carbonate copolymer fiber (into which cells can migrate) attached to an occlusive membrane that does not permit ingrowth of cells and composed of a synthetic bioabsorbable glycolide and lactide copolymer.

After a biodegradable acellular matrix has been selected, a concentrated suspension of autologous passaged fibroblasts is evenly distributed on the surface of the matrix. Using a concentrated suspension is necessary to avoid going beyond the capacity of the matrix to absorb the liquid suspension. For example, a typical distribution of cell suspension using the GORE RESOLUT XT as the matrix comprises applying about 94 μl to about 125 μl of cell suspension having about 2.0×10⁶ cells to about 4.0×10⁶ cells, per square centimeter of matrix. Cells are allowed to attach to the matrix without further addition of media. In a preferred embodiment, incubation of the cells with the matrix occurs at about 37° C. for about 1–2 hours. After at least sixty minutes of incubation, the cells attach to the matrix material. Histological analysis of such matrices after seeding and incubating for at least on hour showed even distribution of cells throughout the matrices. At this time, the culture vessels containing the cell-loaded matrices are supplemented with additional growth medium. Cells are then cultured in the matrix for about 3 to 4 days. The cells are added to the matrix at high density (see above) so as to substantially fill the space within the matrix available for cells. As a result, little to no cell proliferation occurs during this 3–4 day culture period. Methods to establish the appropriate number of autologous passaged fibroblasts to add to any given acellular biodegradable matrix would be known to those in the art. Indeed, it is undesirable for significant cell proliferation to occur during this period because the dividing fibroblasts secrete enzymes (e.g., collagenase) that can degrade or, at least, partially degrade the matrices. The matrix with the cells is then washed at least three times, for 10 minutes per wash, with, e.g., phosphate buffered solution (PBS) to substantially remove immunogenic proteins, e.g., culture medium serum-derived proteins, which can elicit an immune response in the subject. Fresh PBS is used for each washing. The matrix is then incubated twice for at least one hour per incubation in fresh PBS prior to use. After incubation, the matrix comprising autologous fibroblasts is placed on the area of tissue degeneration, or defect, such as, for example, the periodontal pockets, and secured so that it can not be moved from the site.

In the case of sponge matrix (e.g. Collacote®), approximately 1.5–2.0×10⁷ fibroblasts in approximately 1.5 ml of growth medium are seeded onto 2 cm×4 cm thin (approximately 2.5 mm to 3.0 mm thick) sponges. The sponge is then incubated at 37° C. for about 1–2 hours without further addition of medium to allow substantially all the fibroblasts to adhere to the matrix material. After cell adherence, additional growth medium is added to the composition of matrix and fibroblasts which is then incubated at 37° C. for 3–4 days (with daily change of medium). As explained above, little to no cell proliferation occurs during this 3–4 day culture. The composition is then removed from growth medium containing FBS and washed repeatedly (at least 3 times) with FBS-free PBS. After each addition of PBS, the matrix is incubated for 10–20 minutes prior to discarding of the PBS. After the final wash, the composition is either applied directly to the area of the subject requiring tissue regeneration or is transferred to a shipping vial containing a physiological solution (e.g., Kreb's Ringer solution) and shipped (preferably overnight) to a practitioner (e.g., a dentist or physician).

In the case of a membranous matrix (e.g. BioMend™), approximately 3–8×10⁶ fibroblasts in approximately 100 µl of growth medium are seeded onto the 15 mm×20 mm thin (approximately 0.5 to 1.0 mm thick) membranes. The membrane is then incubated at 37° C. for about 30–60 minutes without further addition of medium to allow substantially all the fibroblasts to adhere to the matrix material. After cell adherence, additional growth medium is added to the composition of matrix and fibroblasts which is then incubated at 37° C. for 2–3 days (with daily change of medium). The cells were added to the matrix at high density (see above) so as to substantially fill the space within the matrix available for cells with the same result described above. Washing of the composition and either immediate use or shipping are as described above for the sponge matrices.

In the case of a block matrix such as the above described anorganic matrix (e.g., the Bio-Oss® block) or a demineralized bone matrix (e.g., the Dynagraft™ matrix), approximately 1.2–2.0×10⁷ fibroblasts in approximately 100 µl to 150 µl of growth medium are seeded into 1 cm×1 cm×2 cm cubic blocks of matrix material. Cells are slowly seeded onto one face of the block face. Once the medium and cells have been absorbed into the block, another face of the block is seeded in a similar fashion. The procedure is repeated until all faces of the block have been seeded and the block is fully saturated with medium. Care is taken to avoid adding excess medium and thereby causing leaking out of medium and cells from the block. The composition is then incubated at 37° C. for about 60–120 minutes without further addition of medium to allow substantially all the fibroblasts to adhere to the matrix material. After cell adherence, additional growth medium is added to the composition of matrix and fibroblasts which is then incubated at 37° C. for 2–3 days (with daily change of medium). The cells were added to the matrix at high density (see above) so as to substantially fill the space within the matrix available for cells with the same result described above. Washing of the composition and either immediate use or shipping are as described above for the sponge matrices.

Compositions using Bio-Oss® collagen, RESOLUT, COLLACOTE®, Dynagraft™ as the matrix material have been used to heal extraction sockets of 19 patients after extraction of a tooth. In untreated extraction sockets, the subject's fibroblasts migrate into the sockets approximately 10–14 days after extraction of the tooth and thus the healing process only begins at that time. However, by implanting the compositions containing the patient's fibroblasts into the sockets immediately after extraction of the tooth (e.g., within 1–3 hours of the extraction), the healing process is initiated immediately. Furthermore, by implanting the compositions, shrinkage of the socket (due to collapse of the socket walls), which is generally approximately 30% in untreated sockets, is minimized. It is particularly desirable that socket shrinkage be minimized in cases in which it is proposed to implant a dental prosthesis (e.g., a false tooth) at the site of the extraction at a later date.

The inventors have also found that Bio-Oss® collagen matrices loaded with autologous fibroblasts to be useful in the repair of extraction-associated mandibular and maxillary dental ridge defects. In two patients whose dental ridges had been treated with such compositions, after being in place for 6–18 months, there was no detectable deterioration of the matrix material and the structure resembled normal bone.

In all the compositions used for the above described procedures, fibroblasts obtained from 1 mm punch biopsies of the patients' gum tissues were used and the compositions were shipped to the dentists performing the procedures. The compositions were shaped by the dentist to fit into the extraction sockets. In general, the compositions after shaping had an approximately cylindrical shape with a length of approximately 10 mm and a diameter of approximately 4 mm. At the time of implanting, fragments of the compositions were prepared for histological analysis. In all cases, fibroblast colonization of and proliferation within the matrices was seen by light microscopy.

The above-mentioned advantages (i.e., facile healing and maintenance of socket volume) were seen in all cases. Furthermore, infection of the tissues surrounding the socket, which is a frequently observed sequela of procedures in which extraction sockets are not treated, was not observed in any case. Compositions using Bio-Oss® collagen (2 patients) as the matrix had the advantage of persistence of the matrix material in the sockets longer than those compositions in which the matrix material consisted of collagen only and thus provided physical support for the fibroblasts before full replacement of the matrix material with components endogenous to the patient, e.g., cells and extracellular matrix components.

EXAMPLE III

An Injectable Composition for Correcting Skin Defects and Augmenting Tissue in a Subject As explained above, the present invention extends to an injectable composition for correcting a defect in skin of a subject, or augmenting tissue of a subject, wherein the injectable composition comprises passaged autologous fibroblasts substantially free of immunogenic proteins (e.g., culture medium serum-derived proteins), and a biodegradable, acellular injectable filler material. Examples of skin defects that can be treated with the present invention include scars, particularly facial scars resulting from trauma or acne, or wrinkles. Any of the other skin and other tissue defects listed above can also be treated with the present invention. Furthermore, the present invention can be used to augment tissue in a subject. For example, the injectable composition of the present invention can be injected into the lips of a subject in order to make the lips larger and fuller, or it can be injected below laugh lines to eliminate or diminish them. Furthermore, the compositions can be injected subcutaneously to treat subcutaneous defects that can have arisen from congenital or acquired effects. Fibroblasts are used in the present invention because they can be readily obtained and expanded, and are a cell type normally present beneath the dermis. Fibroblasts taken from a biopsy of the gums, palate, or skin of the subject can be used in the present invention, and can readily obtained using procedures set forth above.

Initially, a dermal fibroblast culture is initiated from a 1 to 5 mm full thickness biopsy specimen of the gums, palate or skin of the subject. Because of the phenomenon of allograft rejection, which is well known to transplantation surgeons and immunologists, it is essential that the cultured fibroblasts be histocompatible with the host. Histocompatibility can be ensured by obtaining a biopsy of the subject to be treated and culturing the fibroblasts from this specimen.

Before the initiation of the culture, the biopsy is washed repeatedly with antibiotic and antifungal agents (see above). The specimen of dermis is then separated into small pieces. The pieces of the specimen are individually placed onto the dry surface of a tissue culture flask and allowed to attach for between about 5 and about 10 minutes, before a small amount of medium is slowly added, taking care not to displace the attached tissue fragments. After about 48 hours of incubation, the flask is fed with additional medium. When a T-25 flask is used to start the culture, the initial amount of medium is about 1.5–2.0 ml. The establishment of a cell line from the biopsy specimen ordinarily takes between about 2 and 3 weeks, at which time the cells can be removed from the initial culture vessel for expansion.

During the early stages of the culture, it is desirable that the tissue fragments remain attached to the culture vessel bottom; fragments that detach should be reimplanted into new vessels. The fibroblasts can be stimulated to grow by a brief exposure to EDTA-trypsin, according to techniques well known to those skilled in the art. The exposure to trypsin is too brief to release the fibroblasts from their attachment to the culture vessel wall.

Immediately after the cultures have become established and are approaching confluence, samples of the fibroblasts can be processed for frozen storage, such as in liquid nitrogen. Presently, numerous methods for successfully freezing cells for later use are known in the art and are included in the present invention. The frozen storage of early rather than late passage fibroblasts is preferred because the number of passages in cell culture of normal human fibroblasts is limited.

The fibroblasts can be frozen in any freezing medium suitable for preserving fibroblasts. A medium consisting of about 70% (v/v) growth medium, about 20% (v/v) fetal bovine serum and about 10% (v/v) dimethylsulfoxide (DMSO) can be used with good effect. DMSO can also be substituted with, for example, glycerol. Thawed cells can be used to initiate secondary cultures to obtain suspensions for use in the same subject without the inconvenience of obtaining a second specimen.

Any tissue culture technique that is suitable for the propagation of dermal fibroblasts from biopsy specimens may be used to expand the cells to practice the invention. Techniques well known to those skilled in the art can be found in R. I. Freshney, Ed., ANIMAL CELL CULTURE: A PRACTICAL APPROACH (IRL Press, Oxford, England, 1986) and R. I. Freshney, Ed., CULTURE OF ANIMAL CELLS: A MANUAL OF BASIC TECHNIQUES, Alan R. Liss & Co., New York, 1987), which are hereby incorporated by reference.

The medium can be any medium suited for the growth of primary fibroblast cultures. The medium can be supplemented with human or non-human serum in an amount of between about 0.0% and about 20% (v/v) to promote growth of the fibroblasts. Higher concentrations of serum promote faster growth of the fibroblasts. An example of medium having application herein comprises glucose DMEM supplemented with about 2 mM glutamine, about 110 mg/L sodium pyruvate, about 10% (v/v) fetal bovine serum and antibiotics ("complete medium"), wherein the concentration of glucose ranges from approximately 1,000 mg/L of medium to 4,500 mg/L of medium, and preferably is 4,500 mg/L. Fibroblasts can also be expanded in serum-free medium (see above). Serum-containing and serum-free media will generally also contain one or more antibiotics such as those listed above.

Autologous fibroblasts can be passaged into new flasks by trypsinization. For expansion, individual flasks are split 1:3. Triple bottom, T-150 flasks, having a total culture area of 450 cm$^2$ are suitable for the practice of the invention. A triple bottom T-150 flask can be seeded with about $1 \times 10^6$ to about $3 \times 10^6$ cells and has a capacity to yield about $8 \times 10^6$ to about $1.0 \times 10^7$ cells. When the capacity of the flask is reached, which typically requires about 5–7 days of culture, the growth medium is replaced by serum-free medium; thereafter the cells are incubated, i.e., held at between about 30° C. and about 37.5° C., for at least 2 hours. The incubation of the cells in serum-free medium substantially removes from the cells proteins that are derived from the xenogeneic (e.g., fetal bovine) serum which, if present, can elicit an immune response in the subject. In a preferred embodiment, serum-free medium comprises glucose DMEM supplemented with about 2 mM glutamine, and about 110 mg/L sodium pyruvate, wherein the concentration of glucose is approximately 1,000 mg/L of medium to approximately 4,500 mg/L of medium, and preferably 4,500 mg/L of medium.

At the end of the incubation in serum-free medium, the cells are removed from the tissue culture flask by trypsin-EDTA; washed extensively by centrifugation and resuspension; and suspended for subsequent use in an injectable composition of the present invention, or for injection into the subject. Five triple bottom T-150 flasks, grown to capacity, yield about $8\times10^6$ to about $1.0\times10^7$ cells per flask which are sufficient to make up about 1.2 to 1.4 ml of cell suspension.

The cells can be transported at on ice 4° C. so long as they are injected within 24–48 hours of their suspension. The cells can be suspended in an appropriate physiological solution with appropriate osmolarity and tested for pyrogens and endotoxin levels, except for the absence of phenol red pH indicator, and the replacement of the fetal bovine serum by the subject's serum for such transportation (transport medium). In another embodiment the cells can be suspended in Krebs-Ringer solution comprising 5% dextrose or any other physiological solution. The cells can be aspirated and injected into the transport medium.

The volume of saline or transport medium in which the cells are suspended is related to such factors as the number of fibroblasts the practitioner desires to inject, the extent of the defects to the subject's skin that are to be corrected, the size or number of the defects that are to be corrected, and the urgency of the subject's desire to obtain the results of the treatment. Moreover, the practitioner can suspend the cells in a larger volume of medium and inject correspondingly fewer cells at each injection site. In an injectable composition of the present invention, the passaged autologous fibroblasts of the present invention are mixed with a biodegradable, acellular injectable filler material in a ratio of approximately 1:1 by volume.

Biodegradable, Acellular Injectable Filler Material

As explained above, an injectable composition of the present invention also comprises a biodegradable, acellular injectable filler material. Numerous types of biodegradable, acellular injectable filler materials are presently available and have applications in the present invention. More specifically, the filler material can be comprised endogenous proteins, such as any type of collagen from the subject. An example of such a filler is "AUTOLOGEN" produced by Collagenesis, Inc. "AUTOLOGEN" is a dispersion of autologous dermal collagen fibers from the subject, and should not elicit an immune response. In order to obtain "AUTOLOGEN" for the subject, a specimen of tissue is obtained from the subject and forwarded to Collagenesis, Inc., where it is turned into "AUTOLOGEN". Approximately a one and a half square inch of tissue yields one cubic centimeter (cc) of "AUTOLOGEN". After "AUTOLOGEN" has been prepared, its concentration can be adjusted depending upon the amount needed to correct defects in the subject's skin, or augment tissue in the subject. In particular, the concentration of "AUTOLOGEN" in the dispersion can be at least about 25 mg/L.

Another example of filler material comprises exogenous proteins, such as any type of collagen. Presently, numerous collagen products are commercially available and have applications in the present invention. Examples of such products are reconstituted bovine collagen products commercially available including, but not limited to, "ZYDERM I", "ZYDERM II" and "ZYPLAST", which comprise reconstituted bovine collagen fibers cross-linked with glutaraldehyde. These three products, which have been approved by the U.S. Food and Drug Administration (FDA) for treating wrinkle lines and depressed scars since 1981, are produced by the Collagen Corporation of Palo Alto, Calif.

Other examples of filler materials having applications in the present invention include, but are not limited to, solubilized gelatin, polyglycolic acid, or cat gut sutures. One particular is a gelatin matrix implant sold under the mark "FIBRIL", which comprises porcine gelatin powder plus o-aminocaproic acid, which are dispersed in a 0.9% (by volume) sodium chloride solution and an aliquot of plasma from the subject, mixed in a 1:1 ratio by volume.

Methods for Correcting a Defect in Skin or Augmenting Tissue

Furthermore, the present invention extends to methods for correcting a defect in skin of a subject, such as scars, wrinkles or any of the other skin, bone or subcutaneous defects, disorders, or diseases listed herein. It can be used for augmenting tissue in the subject, particularly facial tissue, e.g., augmenting the tissue of lips to make the lips appear fuller. One such method of the present invention comprises injecting an effective amount of an injectable composition comprising autologous fibroblasts substantially free of immunogenic proteins (e.g., culture medium serum-derived proteins) and a biodegradable, acellular injectable filler material, into the subject at the site of the skin defect or desired tissue augmentation so that regeneration of tissue at the site is promoted.

Another method encompassed by the present invention comprises the steps of injecting passaged autologous fibroblasts substantially free of immunogenic proteins (e.g., culture medium serum-derived proteins) into the subject at a site of a skin defect or desired tissue augmentation, and injecting a biodegradable, acellular injectable filler material into the site. Preferably, the duration between injecting the autologous fibroblasts into the subject and injecting the biodegradable acellular injectable filler into the subject is about two weeks.

Passaged, autologous fibroblasts substantially free of immunogenic proteins (e.g., culture medium serum-derived proteins) can be readily obtained using procedures set forth above. Furthermore, the various types of biodegradable, acellular filler materials, which have been described in detail above, have applications in the methods described herein.

Injections set forth in the present invention are typically carried out with a hypodermic syringe having a syringe chamber, a piston disposed therein, an orifice communicating with the chamber, and a hypodermic needle is fixed to the orifice. The size of the needle used in a method for correcting a defect in skin of a subject or augmenting tissue in the subject ranges from approximately 30 gauge to approximately 27 gauge. With more viscous compositions needles of, e.g., 14 to 16 gauge can be used.

Initially, the tissue to be injected is prepped with alcohol and stretched to give a taut surface. After the tissue to be injected has been prepped, a syringe is filled with an injectable composition of the present invention, if the first method described above is to be used, or with passaged, autologous fibroblasts substantially free of immunogenic proteins (e.g., culture medium serum-derived proteins) if the second method for correcting skin defects or augmenting tissue is used. The needle is inserted into the tissue as superficially as possible, and the orientation of the bevel is not critical to the success of this method of present invention. The actual injection is made by gentle pressure until a slight blanch is seen in the injected tissue. Multiple serial injections can be made. Approximately two weeks after passaged autologous fibroblasts are injected into the subject's skin, an equal volume of biodegradable, acellular filler is injected using the same procedure as described above into the same location where the passaged autologous fibroblasts were previously injected.

The present invention is not to be limited in scope by the specific embodiments described above, which are intended as illustrations of aspects of the invention. Here functionally equivalent methods and components are within the scope of the invention. Indeed, various modifications of the invention, in addition to those shown and described herein, will become apparent to those skilled in the art from the foregoing description. Such modifications are intended to fall within the scope of the appended claims. Moreover, all cited references are, hereby, incorporated by reference.

What is claimed is:

1. A method of repairing bone tissue in a subject with a bone defect, wherein said method comprises:

a) providing a composition, wherein the composition comprises (i) a biodegradable acellular matrix and (ii) autologous fibroblasts, wherein the composition is substantially free of proteins derived from xenogeneic serum of xenogeneic serum-containing culture medium, wherein said biodegradable acellular matrix, prior to combination with said autologous fibroblasts, comprises one or more substances selected from the group consisting of collagen, glycosaminoglycans, gelatin, polyglycolic acid, cat gut, demineralized bone, hydroxyapatite, and anorganic bone, and wherein and said autologous fibroblasts are added to the matrix at high density and then cultured for up to 4 days, such that sufficient autologous fibroblasts integrate within said biodegradable acellular matrix to substantially fill the space on and within said biodegradable acellular matrix available for cells;

b) identifying a site of a bone defect in said subject; and c) placing the composition on the site so that said bone defect is repaired.

2. The method of claim 1, wherein the bone defect is a dental ridge defect.

3. The method of claim 1, wherein the bone defect is a defect of a mandibular bone.

4. The method of claim 1, wherein the bone defect is a defect of a maxillary bone.

5. The method of claim 1, wherein the bone defect is a defect of a bone selected from the group consisting of an orbital bone, a zygomatic bone, a cranial bone, or a nasal bone.

6. The method of claim 1, wherein the bone defect is a sinus floor defect.

7. The method of claim 1, wherein the bone defect is a non-union defect.

8. The method of claim 7, wherein the non-union defect is a non-union defect of a long bone.

9. The method of claim 1, wherein said biodegradable matrix, prior to combination with said autologous fibroblasts, comprises collagen and glycosaminoglycans, the collagen being cross-linked to the glycosaminoglycans with glutaraldehyde.

10. The method of claim 1, wherein said one or more substances are selected from the group consisting of gelatin, polyglycolic acid, cat gut sutures, demineralized bone, and hydroxyapatite.

11. The method of claim 1, wherein said autologous fibroblasts are from gums, palate, or skin of said subject.

12. The method of claim 1, wherein said one or more substances comprise anorganic bone.

13. The method of claim 12, said one or more substances further comprising collagen.

14. The method of claim 1, wherein the collagen is bovine collagen.

15. The method of claim 1, wherein the collagen is porcine collagen type I or porcine collagen type III.

16. The method of claim 1, wherein said autologous fibroblasts, after being added to the matrix at high density, are cultured for 3 to 4 days.

* * * * *

UNITED STATES PATENT AND TRADEMARK OFFICE
CERTIFICATE OF CORRECTION

PATENT NO. : 6,878,383 B2
DATED : April 12, 2005
INVENTOR(S) : Boss, Jr. et al.

Page 1 of 1

It is certified that error appears in the above-identified patent and that said Letters Patent is hereby corrected as shown below:

<u>Title page,</u>
Item [*] Notice, after "116 days.," insert -- This patent is subject to a terminal disclaimer. --.

<u>Column 25,</u>
Line 30, delete "and".

Signed and Sealed this

Tenth Day of January, 2006

JON W. DUDAS
*Director of the United States Patent and Trademark Office*